United States Patent [19]

Linares et al.

[11] Patent Number: 5,641,479
[45] Date of Patent: Jun. 24, 1997

[54] COSMETIC COMPOSITIONS COMPRISING AN IMIDAZOLIUM DERIVATIVE AND BRANCHED POLYETHYLENE GLYCOL

[75] Inventors: Carlos Gabriel Linares, Stamford; George Endel Deckner, Trumbull; Lucie Anita St. John, Waterbury, all of Conn.

[73] Assignee: Richardson-Vicks Inc., Shelton, Conn.

[21] Appl. No.: 529,403

[22] Filed: Sep. 18, 1995

Related U.S. Application Data

[63] Continuation of Ser. No. 342,672, Nov. 21, 1994, abandoned, which is a continuation of Ser. No. 184,410, Jan. 7, 1994, abandoned, which is a continuation of Ser. No. 7,380, Jan. 21, 1993, abandoned, which is a continuation of Ser. No. 866,735, Apr. 10, 1992, abandoned, which is a continuation-in-part of Ser. No. 654,177, Feb. 12, 1991, abandoned.

[51] Int. Cl.$^6$ ............................... A61K 7/48; A61K 7/50
[52] U.S. Cl. .................... 424/70.21; 424/401; 514/846
[58] Field of Search .................... 424/70.1, 70.11, 424/70.19, 70.21, 70.22, 70.13, 70.17, 78.03, 401; 252/2, 5, 7, 14

[56] References Cited

U.S. PATENT DOCUMENTS

| | | | |
|---|---|---|---|
| 3,957,970 | 5/1976 | Korkis | 514/785 |
| 4,181,634 | 1/1980 | Kennedy | 252/545 |
| 5,192,462 | 3/1993 | Gloor et al. | 252/174.21 |

FOREIGN PATENT DOCUMENTS 250181  12/1987  European Pat. Off. ......... A61K 7/08

OTHER PUBLICATIONS

Application Serial Number 07/675,382 Inventor Date et al. Filing Date Mar. 26, 1991.

Application Serial Number 07/654,147 Inventor Date et al. Filing Date Feb. 12, 1991.

*Crodata*, Crothix bulletin (Jun. 15, 1989).

*Primary Examiner*—Sallie M. Gardner
*Attorney, Agent, or Firm*—Anthony D. Sabatelli; David K. Dabbiere

[57] ABSTRACT

An aqueous foaming cosmetic composition comprising (a) from 0.1 to 7% of an imidazolinium amphoteric surfactant, (b) from about 0.1% to about 5.0% of a polyol alkoxy ester wherein the ratio of (a):(b) is from about 15:1 to about 1:1 and wherein the cleansing composition has a viscosity of at least about 150 cps (Brookfield RVT, Spindle No TB, 10 rpm, 25° C.). The composition has improved foam stability, together with excellent cleansing performance and mildness. It is suitable for use as make-up and facial cleansers, foam bath, shower products, shampoos etc.

15 Claims, No Drawings

COSMETIC COMPOSITIONS COMPRISING AN IMIDAZOLIUM DERIVATIVE AND BRANCHED POLYETHYLENE GLYCOL

This is a continuation of application Ser. No. 08/342,672, filed on Nov. 21, 1994, now abandoned, which is a continuation of application Ser. No. 08/184,410, filed on Jan. 7, 1994, now abandoned, which is a continuation of application Ser. No. 08/007,380, filed Jan. 21, 1993, now abandoned, which is a continuation of application Ser. No. 07/866,735, filed Apr. 10, 1992, now abandoned, which is a continuation-in-part of application Ser. No. 07/654,177, filed Feb. 12, 1991, now abandoned.

TECHNICAL FIELD

The present invention relates to improved cosmetic cleansing compositions, and in particular to foaming cosmetic compositions suitable for cleansing the skin and/or the hair and which may be used, for example, in the form of make-up removal and facial cleansers, bath foams, shower products, shampoos and the like.

BACKGROUND OF THE INVENTION

Foaming cosmetic compositions must satisfy a number of criteria including cleansing power, foaming properties and mildness/low irritancy with respect to the skin, hair and the occular mucosae.

Skin is made up of several layers of cells which coat and protect the keratin and collagen fibrous proteins that form the skeleton of its structure. The outermost of these layers, referred to as the stratum corneum, is known to be composed of 250 A diameter protein bundles surrounded by 80 A thick bilayers of epidermal lipids and water. Anionic surfactants can penetrate the stratum corneum membrane and, by delipidization (i.e. removal of the lipids from the stratum corneum), destroy its integrity. This destruction of the stratum corneum bilayers can lead to dry rough skin and may eventually permit the surfactant to interact with the viable epidermis, creating irritation.

Ideal cosmetic cleansers should cleanse the skin or hair gently, causing little or no irritation without defatting and or drying the skin and without leaving skin taut after frequent use. Most lathering soaps, liquids and bars fail in this respect.

Certain synthetic surfactants are known to be mild. However, a major drawback of most mild synthetic surfactant systems, when formulated for skin cleansing, is poor lather performance compared to the highest bar soap standards (bars which are rich in coconut soap and supernatted). On the other hand, the use of known high sudsing anionic surfactants with lather boosters can yield acceptable lather volume and quality. Unfortunately, however, the highest sudsing anionic surfactants are, in fact, poor in clinical skin mildness. Surfactants that are among the mildest, such as sodium lauryl glyceryl ether sulfonate, (AGS), are marginal in lather. These two facts make the balancing of the surfactant selection and the lather and skin feel benefit a delicate process.

Rather stringent requirements for cosmetic cleansers limit the choice of surface-active agents, and final formulations represent some degree of compromise. Mildness is often obtained at the expense of effective cleansing, or lathering may be sacrificed for either mildness, product stability, or both.

Thus a need exists for foaming cosmetic compositions which will produce a foam which is abundant, stable and of high quality (compactness), which are effective skin and hair cleansers and which are very mild to the skin, hair and occular mucosae.

It has been found that the use of specific polyol alkoxy esters in combination with specific amphoteric surfactants provide cosmetic cleansing compositions with significantly improved dermal mildness benefits and also good physical characteristics such as foaming.

It is therefore an object of the present invention to provide an improved cosmetic cleansing composition which thoroughly cleanses the skin and hair and which is very mild to the skin, hair and occular mucosae.

It is a further object of the present invention to provide an improved cosmetic cleansing composition which is mild and which will produce a foam which is abundant, stable and of high quality, and which effectively cleans skin and hair.

SUMMARY OF THE INVENTION

The present invention relates to foaming cosmetic compositions suitable for cleansing the skin or hair and which may be used as make-up removers and facial cleansers, bath foams, shower products, shampoos, and the like comprising:

(a) from about 0.1% to about 7.0% by weight on a solids basis of an amphoteric surfactant which is an imidazolium derivative of formula I:

wherein $R_1$ is $C_8$–$C_{22}$ alkyl or alkenyl, $R_2$ is hydrogen or $CH_2COOM$, Z is H, $CH_2COOM$, $CH_2CH_2COOM$, or $CH_2CHOHCH_2SO_3M$, Y is H, $CH_2COOM$, $CH_2CH_2COOM$, or $CH_2CHOHCH_2SO_3M$ and M is H, alkali metal, alkaline earth metal, ammonium or alkanol-ammonium;

(b) from about 0.1% to about 5.0% of a polyol alkoxy ester; and (c) from about 60% to about 99.5% water; wherein the ratio of (a):(b) is from about 15:1 to about 1:3 and wherein the cleansing composition has a viscosity of at least about 150 cps (Brookfield RVT, Spindle No TB, 10 rpm, 25° C.).

All concentrations and ratios herein are by weight of total composition and all measurements are at 25° C., unless otherwise specified.

DETAILED DESCRIPTION OF THE INVENTION

The invention relates to a foaming cosmetic composition with superior mildness and excellent lathering characteristics (abundance, quality) and good cleansing ability. The foaming cosmetic composition take the form of a viscous liquid, paste or gel which has the advantage that it can be easily and commercially packaged in and dispensed from pump bottles or from tubes by squeezing. Gel form compositions are defined herein as those which have a viscosity (Brookfield RVT, Spindle No. TB, 10 rpm, 25° C.) of at least 10,000 cps. Preferred from the viewpoint of flowability are gel compositions having a viscosity in the range from about 10,000 to about 50,000 cps, more preferably from about 10,000 to about 20,000 cps. Viscous liquids or pastes are defined herein as those having a viscosity (same conditions) of at least about 150 cps, preferably at least about 500 cps and less than about 10,000 cps, and more preferably between about 5,000 cps and about 9,000 cps.

Surfactant

The essential surfactant component of the compositions of the present invention is an amphoteric surfactant selected from imidazolinium surfactants of formula I

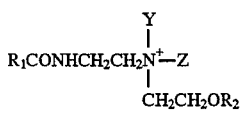

wherein $R_1$ is $C_8$–$C_{22}$ alkyl or alkenyl, $R_2$ is hydrogen or $CH_2COOM$, Z is H, $CH_2COOM$, $CH_2CH_2COOM$, or $CH_2CHOHCH_2SO_3M$, Y is H, $CH_2COOM$, $CH_2CH_2COOM$, or $CH_2CHOHCH_2SO_3M$ and M is H, alkali metal, alkaline earth metal, ammonium or alkanolammonium;

These amphoteric surfactants are present in the compositions of the present invention at a level of from about 0.1% to about 7%, preferably from about 0.1% to about 5%, more preferably from about 0.1% to about 3% and most preferably from about 0.1% to about 2.5%, on a solids basis.

Examples of suitable amphoteric surfactants for use herein include compounds in which $R_1$ is $C_8H_{17}$ (especially iso-capryl), $C_8H_{19}$, $C_{11}H_{23}$ and $C_{12}H_{25}$ alkyl. Especially preferred are the compounds in which $R_1$ is $C_{12}H_{25}$, Z is $CH_2CO_2M$, Y is $CH_2COOM$ and $R_2$ is H. These surfactants are all fully described in *Miranol Products for Cosmetics and Toiletries Technical and Product Development*, Tenth Edition (1987); which is incorporated by reference herein.

It will be understood that a number of commercially-available amphoteric surfactants of this type are manufactured and sold in the form of complexes with anionic surfactants, especially those of the sulfated $C_8$–$C_{18}$ alcohol or $C_8$–$C_{18}$ acyl glyceride types. More preferably, the compositions comprise the surfactant component along with a premix or complex of the optional amphoteric surfactant and anionic surfactant in an equivalent ratio of about 1:1 in order to provide approximate electroneutrality.

In a preferred embodiment of the present invention, the compositions comprise a second amphoteric surfactant being selected from aminoalkanoates of formula 11

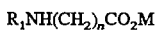

iminodialkanoates of formula III

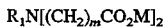

and mixtures thereof, wherein n and m are numbers from 1 to 4, and $R_1$ and M are independently selected from the groups specified in I above.

The compositions herein can also comprise other optional surfactant components, notably, anionic surfactants. It is an important feature of the invention, however, that the combined concentration of the first and the optional second amphoteric surfactants is at least about 30% by weight of the total surfactant concentration, this being important from the viewpoint of achieving optimum lathering characteristics. In preferred compositions, the mixture of the first and second amphoteric surfactants comprises at least about 60%, more preferably at least about 75% by weight of the total surfactant composition.

Examples of suitable optional amphoteric surfactants for use herein include salts, especially the triethanolammonium salts and salts of N-lauryl-beta-aminopropionic acid and N-lauryl-imino-dipropionic acid.

The compositions herein preferably contain from about 1% to about 10% by weight, more preferably from about 1.5% to about 5% by weight of each of the first and second amphoteric surfactants. The weight ratio of first amphoteric surfactant:second amphoteric surfactant is preferably from about 10:1 to about 1:10, more preferably from about 5:1 to about 1:5, and especially from about 1 to about 1:3.

A preferred optional surfactant in the compositions herein is an anionic surfactant. This is preferably present in a level of from about 0.1% to about 10%, more preferably from about 1.0% to about 8%, and especially from about 4% to about 6% by weight. Preferred artionic surfactants for inclusion herein, other than the alkyl and acylglyceride sulfates mentioned above, are the fatty acid condensation products of proteins, degraded proteins or amino acids, or mixtures of such condensation products. In highly preferred embodiments, the fatty acid condensation products are selected from:

(i) condensation products of $C_8$–$C_{12}$, preferably $C_{10}$–$C_{18}$ fatty acids with hydrolysed proteins;

(ii) fatty acid sarconsinates derived from $C_8$–$C_{22}$, preferably $C_{10}$–$C_{18}$ fatty acids; and (iii) mixtures thereof.

However, the total level of surfactant in the compositions herein should generally lie in the range from about 1% to about 20% by weight, preferably from about 1% to about 15% by weight, and especially from about 2% to about 7% by weight.

Polyol Alkoxy Ester

The compositions of the present invention also essentially comprise a polyol alkoxy ester. These materials are nonionic high molecular weight polyhydroxyalkyl derivatives of polyols which have been esterified with a fatty acid material. In other words, these esters include a polyol component, a polyalkoxy component, and a fatty acid component. Examples of polyols which form the basis of these polyol alkoxy esters include polyols having at least 3 hydroxy groups and having from about 3 to about 10 carbon atoms in either a straight or branched chain. Preferably these polyhydroxy compounds have from about 4 to about 8 carbon atoms, either straight or branched chain. Non-limiting examples of polyols which form the basis of these esters include erythritol, threitol, pentaerythritol, xylitol, sorbitol, glucitol, mannitol, and the like. Especially preferred is pentaerythritol.

The polyalkoxy component of these esters include polyethoxy groups (i.e. polyethylene glycol groups), polypropoxy groups (i.e. polypropylene glycol groups), polybutoxy groups (i.e. polybutylene glycol groups), and the like. Preferred derivatives contain polyethoxy groups and polypropoxy. Especially preferred are derivatives containing polyethoxy groups. These polyl alkoxy esters can be prepared from the reaction of the desired polyol with an alkoxylation agent until the desired degree of derivatization has been achieved, i.e. until the desired number of moles of the alkoxy group has been incorporated. Non-limiting examples of alkoxylation agents include ethylene oxide, propylene oxide, butylene oxide, and the like. The polyol alkoxy esters preferably have a mole ratio of polyol to akoxy group of from about 1:50 to about 1:250, more preferably from about 1:100 to about 1:200, and most preferably from about 1:125 to about 1:175.

The fatty acid component of these polyol alkoxy esters include straight or branched chain, saturated or unsaturated fatty acids having from about 8 to about 30 carbon atoms.

These esters have high molecular weights ranging from about 4000 to about 8000 and preferably from about 6000 to about 8000. A highly preferred polyol alkoxy ester is available from Croda, Inc. under the trade name Crothix. This material, which is also known as PEG-150 petaerythritol tetra stearate, is synthesized by the reaction of petaerythritol with ethylene oxide to a mean adduct level of 150 moles, followed by esterification with stearic acid.

The polyol alkoxy ester is present in the composition at a level of from about 0.1% to about 5%, preferably from about 0.5% to about 3%, and most preferably from about 1% to about 2%.

The amphoteric surfactant and polyol alkoxy ester are present in a ratio of amphoteric surfactant:polyol alkoxy ester of from about 10:1 to about 1:3, preferably from about 5:1 to about 1:3 and most preferably from about 3:1 to about 1:3.

Optional Components

The compositions of the invention may also contain additional thickeners at a level preferably from about 0.1% to about 10%, more preferably from about 0.1% to about 5%, and especially from about 0.3% to about 4%. The thickener preferably has a viscosity (1% aqueous solution, 25° C., Brookfield RVT Spindle No TB, 5 rpm) of at least about 4000 cps, more preferably at least about 10,000 cps.

Neutralizing agents suitable for use in neutralizing acidic group containing hydrophilic thickeners herein including sodium hydroxide, potassium hydroxide, ammonium hydroxide, monoethanolamine, diethanlolamine and triethanolamine.

The compositions of the invention can optionally include a hair or skin moisturizer. The preferred level of moisturizer is from about 1% to about 20% by weight. In preferred embodiments, the moisturizer is nonocclusive and is selected from:

1. water-soluble liquid polyols;
2. essential amino acid compounds found naturally occurring in the stratum corneum of the skin; and
3. water-soluble nonocclusives and mixtures thereof.

Some examples of more preferred nonocclusive moisturizers are glycerine, polyethylene glycol, propylene glycol, sorbitol, polyethylene glycol and propylene glycol esters of methyl glucose (e.g. methyl gluxan-20), polyethylene glycol and propylene glycol esters of lanolin alcohol (e.g. Solulan-75), sodium pyrrolidone carboxylic acid, lactic acid, urea, L-proline, guanidine, pyrrolidone and mixtures thereof. Of the above, glycerine is highly preferred.

Examples of other water-soluble nonocclusive moisturizers include water-soluble hexadecyl, myristyl, isodecyl or isopropyl esters of adipic, lactic, oleic, stearic, isostearic, myristic or linoleic acids, as well as many of their corresponding alcohol esters (sodium isostearoyl-2-lactylate, sodium capryl lactylate), hydrolyzed protein and other collagen-derived proteins, aloe vera gel and acetamide MEA.

The compositions of the invention can additionally comprise from about 0.05% to about 5% by weight of cationic or nonionic polymeric hair or skin conditioning agents. Representatives classes of polymeric hair or skin conditioning agents include cationic and nonionic polysaccharides; cationic and nonionic homopolymers and copolymers derived from acrylic and/or methacrylic acid; cationic and nonionic cellulose resins; cationic copolymers of dimethyl-diallylammonium chloride and acrylic acid; cationic homopolymers of dimethyldiallylammonium chloride; cationic polyalkylene and ethoxypolyalkene imines, and mixtures thereof.

By way of exemplification, cationic polymeric conditioning agents preferred for use herein include cationic guar gums such as hydroxypropyl trimethyl ammonium guar gum (d.s. of from 0.11 to 0.22) available commercially under the trade names Jaguar C-14-S(RTM) and Jaguar C-17(RTM), and also Jaguar C-16(RTM), which contains hydroxypropyl substituents (d.s. of from 0.8–1.1) in addition to the above-specified cationic groups, and quatnerized cellulose esters available commercially under the trade names Ucare Polymer JR and Celquat. Other suitable cationic polymers are homopolymers of dimethyldiallylammonium chloride available commercially under the trade name Merquat 100, copolymers of dimethyl aminoethylmethacrylate and acrylamide, copolymers of dimethyldiallylammonium chloride and acrylamide, available commercially under the trade names Merquat 550 and Merquat S, quaternized vinyl pyrrollidone acrylate or methacrylate copolymers of amino alcohol available commercially under the trade name Gafquat, and polyalkylenimines such as polyethylenimime and ethoxylated polyethylenimine.

A number of additional optional materials can be added to the compositions of the invention. Such materials include keratolytic agents such as salicylic acid; proteins and polypeptides and derivatives thereof; water-soluble or solubilizable preservatives such as Germall 115, methyl, ethyl, propyl and butyl esters of hydroxybenzoic acid, EDTA, Euxyl (RTM) K400, Bronopol (2-bromo-2-nitropropane-1, 3-diol); antiobacterials such as Irgasan (RTM), phenoxyethanol and phenoxypropanol (preferably at levels of from about 0.2% to about 5%); other moisturizing agents such as hyaluronic acid, chitin, and starchgrafted sodium polyacrylates such as Sanwet (RTMO IM-1000, IM-1500 and IM-2500 available from Celanese Superabsorbent Materials, Portsmith, Va., USA and described in U.S. Pat. No. 4,076, 663; colouring agents; Pearling agents; perfumes and perfume solubilizers etc. Water is also present at a level of from about 60% to about 99.5%, preferably from about 70% to about 95% by weight of the compositions herein.

The pH of the compositions is preferably from about 4 to about 9, more preferably from about 4.5 to about 7.

The following examples further describe and demonstrate embodiments within the scope of the present invention. The examples are given solely for the purpose of illustration and are not to be construed as limitations of the present invention, as many variations thereof are possible without departing from the spirit and scope of the invention.

Ingredients are identified by chemical or CTFA name.

Example I

A facial cleansing composition of the present invention is made as follows:

| Ingredient | % w/w |
| --- | --- |
| Phase A | |
| Water | q.s. |
| Polyquaternium - 10 | 0.50 |
| Phase B | |
| Potassium Coco Hydrolyzed Animal Protein[2] | 15.0 |

| Ingredient | % w/w |
| --- | --- |
| Amphoteric Surfactant I[3] | 5.1 |
| Amphoteric Surfactant II[4] | 6.8 |
| Amphoteric Surfactant III[5] | 7.3 |
| Phase C | |
| Glycerin | 3.0 |
| Polyol Alkoxy Ester[6] | 1.6 |
| PEG-120 Methyl Glucose Dioleate[7] | 0.6 |
| Phase D | |
| Preservative (phenoxyethanol) | 0.4 |
| Phase | |
| Water | 1.0 |
| Na₄EDTA | 0.1 |

[1] Available as Polymer JR 400
[2] Available as Lamepon S
[3] Cocoamphocarboxyglycinate (and) Na Lauryl Sulfate (and) Hexylene Glycol available as Miranol 2MCA MOD
[4] Na Lauryl Sarcosinate available as Hamposyl - L-30
[5] Na Lauriminodipropionate available as Mirataine H2C-HA
[6] Available As Crothix
[7] Available as Glucamate DOE-120

The water is heated to 65° C. and the polyquaternium-10 is added to the water to form Phase A. The Phase B ingredients are added sequentially to this phase. Separately, the Phase C components are heated to 65° C. Phase C is combined with this mixture and then cooled to 40° C. Phase D and Phase E are added to this mix to form the resultant cosmetic composition.

Application of approximately 2 grams of the resulting gel/viscous liquid with water is useful for topical application as a cleanser to remove, for example, dirt and oil as well as difficult to remove make-up, waterproof mascara and the like.

The water is heated to 65° C. and the polyquaternium-10 is added to the water to form Phase A. The Phase B ingredients are added sequentially to this phase. Separately, the Phase C components are heated to 65° C. Phase C is combined with this mixture and then cooled to 40° C. Phase D and Phase E are added to this mix to form the resultant cosmetic composition.

Application of approximately 2 grams of the resulting gel/viscous liquid with water is useful for topical application as a cleanser to remove, for example, dirt and oil as well as difficult to remove make-up, waterproof mascara and the like.

Example II

A facial cleansing composition of the present invention is made by combining the following ingredients utilizing conventional mixing techniques as described above in Example I.

| Ingredient | % w/w |
| --- | --- |
| Phase A | |
| Water | q.s. |
| Polyquaternium - 10[1] | 0.50 |
| Phase B | |
| Amphoteric Surfactant I[2] | 15.1 |
| Amphoteric Surfactant II[3] | 4.0 |
| Phase C | |
| Glycerin | 3.0 |
| Polyol Alkoxy Ester[4] | 1.6 |
| PEG-120 Methyl Glucose Dioleate[5] | 0.6 |
| Phase D | |
| Preservative (phenoxyethanol) | 0.4 |
| Phase E | |
| Water | 1.0 |
| Na₄EDTA | 0.1 |

[1] Available as Polymer JR 400
[2] Na Lauriminodipropionate available as Mirataine H2C—HA
[3] Cocoamphocarboxyglycinate (and) Na Lauryl Sulfate (and) Hexylene Glycol available as Miranol 2MCA MOD
[4] Available as Crothix
[5] Available as Glucamate DOE-120

Application of approximately 2 grams of the resulting gel/viscous liquid with water is useful for topical application as a cleanser to remove, for example, dirt and oil as well as difficult to remove make-up, waterproof mascara and the like.

Example III

A facial cleansing composition of the present invention is made by combining the following ingredients utilizing conventional mixing techniques as described above in Example I.

| Ingredient | % w/w |
| --- | --- |
| Phase A | |
| Water | q.s |
| Polyquaternium - 10[1] | 0.50 |
| Phase B | |
| Amphoteric Surfactant I[2] | 15.1 |
| Amphoteric Surfactant II[3] | 4.0 |
| Phase C | |
| Glycerin | 3.0 |
| Polyol Alkoxy Ester[4] | 1.0 |
| Na Acrylate/Stearate 20 Methacrylate polymer[5] | 3.0 |
| Phase D | |
| Preservative | 0.4 |
| Phase E | |
| Water | 1.0 |
| Na₄EDTA | 0.1 |

[1] Available as Polymer JR 400
[2] Na Lauriminodipropionate available as Deriphat 160C
[3] Cocoamphocarboxyglycinate (and) Na Lauryl Sulfate (and) Hexylene Glycol available as Miranol 2MCA MOD
[4] Available as Crothix
[5] Available as Aculyn 22

Application of approximately 2 grams of the resulting gel/viscous liquid with water is useful for topical application as a cleanser to remove, for example, dirt and oil as well as difficult to remove make-up, waterproof mascara and the like.

Example IV

A facial cleansing composition of the present invention is made by combining the following ingredients utilizing conventional mixing techniques as described above in Example I.

| Ingredient | % w/w |
|---|---|
| Phase A | |
| Water | q.s. |
| Polyquaternium - 10[1] | 0.50 |
| Phase B | |
| Amphoteric Surfactant I[2] | 8.0 |
| Amphoteric Surfactant II[3] | 8.0 |
| Phase C | |
| Glycerin | 15.0 |
| Polyol Alkoxy Ester[4] | 1.5 |
| PEG-120 Methyl Glucose Dioleate[5] | 0.5 |
| Phase D | |
| Preservative (phenoxyethanol) | 0.4 |
| Phase E | |
| Water | 1.0 |
| Na$_4$EDTA | 0.1 |

[1] Available as Polymer JR 400
[2] Lauroamphodiacetate (and) Na Trideceth Sulfate available as Miranol BT
[3] Na Lauriminodipropionate available as Mirataine H2C-HA
[4] Available as Crothix
[5] Available as Glucomate DOE-120

Application of approximately 2 grams of the resulting gel/viscous liquid with water is useful for topical application as a cleanser to remove, for example, dirt and oil as well as difficult to remove make-up, waterproof mascara and the like.

What is claimed:

1. A foaming cosmetic cleansing composition comprising:

(a) from about 0.1% to about 7.0% by weight on a solids basis of an amphoteric surfactant which is an imidazolinium derivative of formula I $$\underset{\substack{|\\CH_2CH_2OR_2}}{R_1CONHCH_2CH_2\overset{Y}{\overset{|}{N^+}}-Z} \qquad I$$

wherein $R_1$ is $C_8$–$C_{22}$ alkyl or alkenyl, $R_2$ is hydrogen or $CH_2COOM$, Z is H, $CH_2COOM$, $CH_2CH_2COOM$, or $CH_2CHOHCH_2SO_3M$, Y is H, $CH_2COOM$, $CH_2CH_2COOM$, or $CH_2CHOHCH_2SO_3M$ and M is H, alkali metal, alkaline earth metal, ammonium or alkanolammonium;

(b) from about 0.1% to about 5.0% of a polyol alkoxy ester wherein the polyols which form the basis for the ester are selected from the group consisting of erythritol, threitol, pentaerythritol, xylitol, glucitol and mannitol; and (c) from about 60% to about 99.5% water;

wherein the ratio of (a):(b) is from about 15:1 to about 1:1 and wherein the cleansing composition has a viscosity of at least about 150 cps (Brookfield RVT, Spindle No TB, 10 rpm, 25° C.).

2. A cosmetic composition according to claim 1 which further comprises from about 0.5% to about 16% by weight of an amphoteric surfactant selected from the group consisting of aminoalkanoates of formula II $$R_1NH(CH_2)_nCO_2M \qquad II$$

iminodialkanoates of formula III $$R_1N[(CH_2)_mCO_2M]_2 \qquad III$$

and mixtures thereof, wherein $R_1$ is $C_{8-22}$ alkyl or alkenyl and M is H, alkali metal, alkaline earth metal, ammonium or alkanol ammonium; and wherein n and m are numbers from 1 to 4, and wherein the sum of the percentages by weight of the amphoteric surfactant I and the amphoteric surfactant selected from the group consisting of II, III and mixtures thereof comprises at least about 30% by weight of the total surfactant component.

3. A cosmetic composition according to claim 2 which comprises from about 0.5% to about 2.0% of the polyol alkoxy ester and wherein the total surfactant concentration is from about 1% to about 20% by weight of the cosmetic composition and wherein said polyol alkoxy ester includes a polyol component, a polyalkoxy component and a fatty acid component, the polyol component having at least 3 hydroxy groups and from about 3 to about 10 carbon atoms in either a straight or branched chain.

4. A cosmetic composition according to claim 3 wherein the ratio of amphoteric surfactant:polyol alkoxy ester is from about 10:1 to about 1:3 and which further comprises from about 1% to about 10% by weight of the amphoteric surfactant I and from about 1% to about 10% by weight of the amphoteric surfactant selected from the group consisting of II, III and mixtures thereof.

5. A cosmetic composition according to claim 4 wherein the weight ratio of the amphoteric surfactant I: the amphoteric surfactant selected from the group consisting of II, III and mixtures thereof is from about 10:1 to about 1:10.

6. A cosmetic composition according to claim 5 wherein the weight ratio of first amphoteric surfactant:second amphoteric surfactant is from about 3:1 to about 1:3, and wherein the composition additionally comprises from about 0.1% to about 10%, by weight of anionic surfactant.

7. A cosmetic composition according to claim 6 wherein the ratio of amphoteric surfactant: polyol alkoxy ester is from about 3:1 to about 1:3.

8. A cosmetic composition according to claim 7 wherein the anionic surfactant is a fatty acid condensation product selected from the group consisting of:

(i) a condensation product of $C_8$–$C_{12}$ fatty acids with hydrolysed proteins, (ii) fatty acid sarcosinates derived from $C_8$–$C_{22}$ fatty acids, and (iii) mixtures thereof and further wherein the polyol alkoxy esters have a mole ratio of polyol to alkoxy group of from about 1:50 to about 1:250.

9. A cosmetic composition according to claim 8 having a viscosity of from about 150 to about 20,000 cps (Brookfield RVT, Spindle No. TB, 10 rpm, 25° C.) and wherein the polyol alkoxy ester is PEG-150 petaerythritol tetra stearate and wherein the condensation product is condensation product of a $C_{10}$–$C_{18}$ fatty acid with hydrolyzed proteins and the fatty acid sarcosinater is derived from $C_{10}$–$C_{18}$ fatty acids.

10. A cosmetic composition according to claim 9 wherein the composition further comprises from about 1% to about 20% of a hair or skin moisturizer.

11. A cosmetic composition according to claim 10 wherein the moisturizer is nonocclusive and is selected from the group consisting of:

(i) water-soluble liquid polyols;

(ii) essential amino acid compounds found in the stratum corneum of the skin; and (iii) water-soluble nonpolyol, nonocclusives and mixtures thereof.

12. A cosmetic composition according to claim 11 wherein the moisturiser is selected from the group consisting of glycerin, polyethylene glycol, propylene glycol, sorbitol, polyethylene glycol and propylene glycol esters of methyl glucose, polyethylene glycol and propylene glycol esters of lanolin alcohol, sodium pyrrolidone carboxylic acid, lactic acid, L-proline and mixtures thereof.

13. A cosmetic composition according to claim 12 wherein the moisturiser is glycerin.

14. A cosmetic composition according to claim 13 additionally comprising from abut 0.05% to about 5% by weight of a cationic or nonionic polymeric hair or skin conditioning agent.

15. A cosmetic composition according to claim 14 wherein the polymeric hair or skin conditioning agent is selected from the group consisting of cationic and nonionic polysacharides; cationic and nonionic homopolymers and copolymers containing acrylic and/or methacrylic acid; cationic and nonionic cellulose resins; cationic copolymers of dimethyldiallylammonium chloride and acrylic acid; cationic homopolymers of dimethyldiallylammonium chloride; cationic polyalkylene and ethoxypolyalkylene imines, and mixtures thereof.

* * * * *